United States Patent
Sund, Sr. et al.

(10) Patent No.: US 10,813,563 B2
(45) Date of Patent: Oct. 27, 2020

(54) FLUORESCENCE BASED FLOW IMAGING AND MEASUREMENTS

(71) Applicant: SCINOVIA, CORP., Sheridan, WY (US)

(72) Inventors: James Bradley Sund, Sr., Raleigh, NC (US); David S. Cohen, Chapel Hill, NC (US)

(73) Assignee: SCINOVIA CORP., Sheridan, WY (US)

( * ) Notice: Subject to any disclaimer, the term of this patent is extended or adjusted under 35 U.S.C. 154(b) by 371 days.

(21) Appl. No.: 15/863,338

(22) Filed: Jan. 5, 2018

(65) Prior Publication Data

US 2018/0125378 A1 May 10, 2018

Related U.S. Application Data

(63) Continuation of application No. PCT/US2016/041045, filed on Jul. 6, 2016.

(Continued)

(51) Int. Cl.
*G06K 9/00* (2006.01)
*A61B 5/0275* (2006.01)
(Continued)

(52) U.S. Cl.
CPC .......... *A61B 5/0275* (2013.01); *A61B 5/0071* (2013.01); *A61B 5/0261* (2013.01);
(Continued)

(58) Field of Classification Search
None
See application file for complete search history.

(56) References Cited

U.S. PATENT DOCUMENTS 7,881,777 B2 * 2/2011 Docherty ............... A61B 1/042
424/9.6
8,285,366 B2 * 10/2012 Hyde ..................... A61B 34/30
600/476

(Continued)

FOREIGN PATENT DOCUMENTS

DE 10120980 A1 11/2002
DE 102008040803 A1 2/2010
(Continued)

OTHER PUBLICATIONS

Frenzel, H., et al., "In vivo perfusion analysis of normal and dysplastic ears and its implication on total auricular reconstruction", Journal of Plastic, Reconstructive & Aesthetic Surgery, 2008, pp. S21-S28, vol. 61.

(Continued)

*Primary Examiner* — Shervin K Nakhjavan
(74) *Attorney, Agent, or Firm* — NK Patent Law

(57) ABSTRACT

Fluorescence based tracking of a light-emitting marker in a bodily fluid stream is conducted by: providing a light-emitting marker into a fluid stream; establishing field of view monitoring by placement of a sensor, such as a high speed camera, at a region of interest; recording image data of light emitted by the marker at the region of interest; determining time characteristics of the light output of the marker traversing the field of view; and calculating flow characteristics based on the time characteristics. Furthermore generating a velocity vector map may be conducted using a cross correlation technique, leading and falling edge considerations, subtraction, and/or thresholding.

16 Claims, 6 Drawing Sheets

Related U.S. Application Data

(60) Provisional application No. 62/189,126, filed on Jul. 6, 2015.

(51) Int. Cl.

| | | |
|---|---|---|
| *A61B 5/00* | (2006.01) | |
| *G01F 1/00* | (2006.01) | |
| *G06T 7/246* | (2017.01) | |
| *G06T 7/254* | (2017.01) | |
| *A61B 5/026* | (2006.01) | |
| *A61M 5/00* | (2006.01) | |
| *G06T 5/00* | (2006.01) | |
| *G06T 5/20* | (2006.01) | |
| *G06T 7/00* | (2017.01) | |
| *G01F 1/708* | (2006.01) | |
| *A61B 90/00* | (2016.01) | |

(52) U.S. Cl.
CPC .......... *A61B 5/7225* (2013.01); *A61B 5/7246* (2013.01); *A61M 5/007* (2013.01); *G01F 1/00* (2013.01); *G06T 5/002* (2013.01); *G06T 5/20* (2013.01); *G06T 7/0016* (2013.01); *G06T 7/246* (2017.01); *G06T 7/248* (2017.01); *G06T 7/254* (2017.01); *A61B 2090/3933* (2016.02); *A61B 2090/3941* (2016.02); *A61B 2576/00* (2013.01); *G01F 1/7086* (2013.01); *G06T 2207/10016* (2013.01); *G06T 2207/10024* (2013.01); *G06T 2207/10064* (2013.01); *G06T 2207/20224* (2013.01); *G06T 2207/30104* (2013.01); *G06T 2207/30204* (2013.01)

(56) References Cited

U.S. PATENT DOCUMENTS

| | | | | |
|---|---|---|---|---|
| 9,523,682 | B2* | 12/2016 | Huang | G01N 33/54366 |
| 10,000,804 | B2* | 6/2018 | Cao | B01L 3/502761 |
| 10,180,398 | B2* | 1/2019 | Sinclair | G01N 15/1427 |
| 2004/0097805 | A1* | 5/2004 | Verard | A61B 1/00071 |
| | | | | 600/428 |
| 2005/0020928 | A1* | 1/2005 | Arsenault | A61B 5/02 |
| | | | | 600/504 |
| 2005/0182434 | A1* | 8/2005 | Docherty | A61B 1/042 |
| | | | | 606/170 |
| 2006/0134002 | A1* | 6/2006 | Lin | A61K 49/0032 |
| | | | | 424/9.6 |
| 2008/0019921 | A1* | 1/2008 | Zhang | A61K 49/0004 |
| | | | | 424/9.6 |
| 2008/0097222 | A1* | 4/2008 | Pertsov | A61B 5/0059 |
| | | | | 600/476 |
| 2008/0281205 | A1* | 11/2008 | Naghavi | A61B 8/12 |
| | | | | 600/458 |
| 2010/0094133 | A1* | 4/2010 | Yoshiara | A61B 8/08 |
| | | | | 600/453 |
| 2010/0305454 | A1* | 12/2010 | Dvorsky | A61B 5/0059 |
| | | | | 600/476 |
| 2011/0044910 | A1* | 2/2011 | Lin | A61B 5/0059 |
| | | | | 424/9.6 |
| 2011/0063427 | A1* | 3/2011 | Fengler | A61B 1/04 |
| | | | | 348/65 |
| 2011/0117028 | A1* | 5/2011 | Zharov | A61B 5/0059 |
| | | | | 424/9.36 |
| 2012/0004716 | A1* | 1/2012 | Langhammer | A61N 1/0529 |
| | | | | 607/148 |
| 2013/0015345 | A1* | 1/2013 | Vertes | H01J 49/0404 |
| | | | | 250/282 |
| 2013/0230464 | A1* | 9/2013 | Yi | A61K 49/0056 |
| | | | | 424/9.6 |
| 2013/0253895 | A1 | 9/2013 | Okell et al. | |
| 2014/0171764 | A1* | 6/2014 | Kim | A61B 5/0071 |
| | | | | 600/317 |
| 2015/0297086 | A1* | 10/2015 | Hong | G01N 21/6428 |
| | | | | 600/431 |
| 2017/0100037 | A1* | 4/2017 | Harmelin | A61B 5/0071 |

FOREIGN PATENT DOCUMENTS

| | | |
|---|---|---|
| DE | 102009010446 A1 | 9/2010 |
| RU | 2506896 C2 | 2/2014 |
| WO | WO2009127972 A2 | 10/2009 |
| WO | 2012038824 A1 | 3/2012 |

OTHER PUBLICATIONS

Holm, C., et al., "Intraoperative evaluation of skin-flap viability using laser-induced fluorescence of indocyanine green", British Journal of Plastic Surgery, 2002, pp. 635-644, vol. 55.

EPO, Extended European Search Report for European Patent Application No. 16821893.1, dated Feb. 13, 2019.

ISA/RU, International Search Report and Written Opinion of PCT Patent Application No. PCT/US2016/041045, dated Sep. 8, 2016.

WIPO, International Preliminary Report on Patentability of PCT Patent Application No. PCT/US2016/041045, dated Jan. 9, 2018.

* cited by examiner

FLUORESCENCE BASED FLOW IMAGING AND MEASUREMENTS

CROSS-REFERENCE TO RELATED APPLICATION

This application is a continuation of International Patent Application Serial No. PCT/US2016/041045, entitled "FLUORESCENCE BASED FLOW IMAGING AND MEASUREMENTS," filed Jul. 6, 2016, which claims the benefit of priority of U.S. provisional patent application No. 62/189,126, titled "FLUORESCENCE BASED FLOW IMAGING AND MEASUREMENTS," filed on Jul. 6, 2015. Each above-reference application is incorporated herein in its entirety by this reference.

TECHNICAL FIELD

The present disclosure relates to fluorescence based imaging and measurements. More particularly, the present disclosure relates to determining flow characteristics such as velocity in bodily vessels such as blood vessels.

BACKGROUND

Fluorescent markers have been used for basic imaging of bodily structures, but improvements are needed in determining flow characteristics in such bodily fluids as blood.

SUMMARY

This summary is provided to introduce in a simplified form concepts that are further described in the following detailed descriptions. This summary is not intended to identify key features or essential features of the claimed subject matter, nor is it to be construed as limiting the scope of the claimed subject matter.

According to at least one embodiment, a method of fluorescence based tracking of a light-emitting marker in a bodily fluid stream includes: providing a light-emitting marker into a bodily fluid stream; monitoring, with a sensor, a region of interest traversed by the bodily fluid stream; recording data generated by the sensor; determining time characteristics of the recorded data; and calculating flow characteristics based on the time characteristics.

In at least one example, the sensor includes a camera, and the recorded data comprises motion video data.

In at least one example, the method further includes: dividing the motion video data into kernels; identifying which of the kernels receive some portion of the light-emitting marker using an intensity threshold; computing, for each identified kernel, an intensity signal data set including information of mean light intensity versus time; performing smoothing on each intensity signal data set; calculating a lag time between the intensity signal data sets of neighboring identified kernels using cross-correlation; using a spatial resolution and the lag time, calculating velocity vectors; summing the velocity vectors of neighboring kernels to create a resultant velocity vector; and generating a velocity map from the resultant velocity vectors for all kernels.

In at least one example, performing smoothing on each intensity signal data set includes time window averaging.

In at least one example, performing smoothing on each intensity signal data set includes using a filter.

In at least one example, wherein performing smoothing on each intensity signal data set includes using a Gaussian filter.

In at least one example, the method further includes: dividing the motion video data into kernels; identifying which of the kernels receive some portion of the light-emitting marker using an intensity threshold; computing, for each identified kernel, an intensity signal data set including information of mean light intensity versus time; performing smoothing on each intensity signal data set; for each particular identified kernel, finding segments in which a slope of the intensity signal data set rises for a minimum consecutive number of frames or falls for a minimum consecutive number of frames, which segments occur when a leading edge or falling edge of a portion of the light-emitting marker passes through the identified kernel; searching the intensity signal data sets of neighboring identified kernels for a rising or falling segment of similar length; calculating a lag time between segments in the particular identified kernel and segments in the neighboring identified kernels; using a spatial resolution and the lag time, calculating velocity vectors; summing the velocity vectors of neighboring kernels to create a resultant velocity vector; and generating a velocity map from the resultant velocity vectors for all kernels.

In at least one example, performing smoothing on each intensity signal data set includes time window averaging. In at least one example, performing smoothing on each intensity signal data set includes using a filter. In at least one example, performing smoothing on each intensity signal data set includes using a Gaussian filter.

In at least one example, the method further includes: calculating a difference frame by subtracting a frame of the motion video data from a consecutive frame of the motion video data; applying a threshold the difference frame to eliminate pixels therein below a specified intensity value; calculating a pixel size of a remaining blob in the difference frame in a direction of blood flow; calculating a size of the remaining blob using the pixel size and a spatial resolution; and calculating a velocity by using a distance traveled by the remaining and a time between frames.

In at least one example, the method further includes: dividing the motion video data into frames each including pixels; identifying which of the pixels receive some portion of the light-emitting marker using an intensity threshold; creating a logical frame in which a respective indicator for each pixel can be set as true or false; setting the indicators of the identified pixels as true; setting the indicators of all other pixels as false; calculating a difference frame by subtracting a first logical frame from a second logical frame such that the difference frame includes pixels that reached the specified threshold after a time of the first logical frame; finding length in pixels of the remaining blob in the difference frame in a direction of blood flow; converting the length in pixels of the difference frame to physical distance using the spatial resolution; and calculating velocity by dividing the physical distance by a time between frames.

According to at least one embodiment, a system for fluorescence based tracking of a light-emitting marker in a bodily fluid stream includes: a delivery apparatus configured to provide a light-emitting marker into a bodily fluid stream; a sensor configured to monitor a region of interest traversed by the bodily fluid stream; and a computing device configured to: record data generated by the sensor; determine time characteristics of the recorded data; and calculate flow characteristics based on the time characteristics.

In at least one example, the sensor includes a camera, and the recorded data includes motion video data.

In at least one example, the computing device is further configured to: divide the motion video data into kernels;

identify which of the kernels receive some portion of the light-emitting marker using an intensity threshold; compute, for each identified kernel, an intensity signal data set including information of mean light intensity versus time; perform smoothing on each intensity signal data set; calculate a lag time between the intensity signal data sets of neighboring identified kernels using cross-correlation; using a spatial resolution and the lag time, calculate velocity vectors; sum the velocity vectors of neighboring kernels to create a resultant velocity vector; and generate a velocity map from the resultant velocity vectors for all kernels.

In at least one example, the computing device performs smoothing on each intensity signal data set by time window averaging. In at least one example, the computing device performs smoothing on each intensity signal data set by using a Gaussian filter.

In at least one example, the computing device is further configured to: divide the motion video data into kernels; identify which of the kernels receive some portion of the light-emitting marker using an intensity threshold; compute, for each identified kernel, an intensity signal data set including information of mean light intensity versus time; perform smoothing on each intensity signal data set; for each particular identified kernel, find segments in which a slope of the intensity signal data set rises for a minimum consecutive number of frames or falls for a minimum consecutive number of frames, which segments occur when a leading edge or falling edge of a portion of the light-emitting marker passes through the identified kernel; search the intensity signal data sets of neighboring identified kernels for a rising or falling segment of similar length; calculate a lag time between segments in the particular identified kernel and segments in the neighboring identified kernels; use a spatial resolution and the lag time to calculate velocity vectors; sum the velocity vectors of neighboring kernels to create a resultant velocity vector; and generate a velocity map from the resultant velocity vectors for all kernels.

In at least one example, the computing device is further configured to: calculate a difference frame by subtracting a frame of the motion video data from a consecutive frame of the motion video data; apply a threshold the difference frame to eliminate pixels therein below a specified intensity value; calculate a pixel size of a remaining blob in the difference frame in a direction of blood flow; calculate a size of the remaining blob using the pixel size and a spatial resolution; and calculate a velocity by using a distance traveled by the remaining blob and a time between frames.

In at least one example, wherein the computing device is further configured to: divide the motion video data into frames each including pixels; identify which of the pixels receive some portion of the light-emitting marker using an intensity threshold; create a logical frame in which a respective indicator for each pixel can be set as true or false; set the indicators of the identified pixels as true; set the indicators of all other pixels as false; calculate a difference frame by subtracting a first logical frame from a second logical frame such that the difference frame includes pixels that reached the specified threshold after a time of the first logical frame; find length in pixels of the remaining blob in the difference frame in a direction of blood flow; convert the length in pixels of the difference frame to physical distance using the spatial resolution; and calculate velocity by dividing the physical distance by a time between frames.

BRIEF DESCRIPTION OF THE DRAWINGS

The previous summary and the following detailed descriptions are to be read in view of the drawings, which illustrate particular exemplary embodiments and features as briefly described below. The summary and detailed descriptions, however, are not limited to only those embodiments and features explicitly illustrated.

DETAILED DESCRIPTIONS

Figure 1:
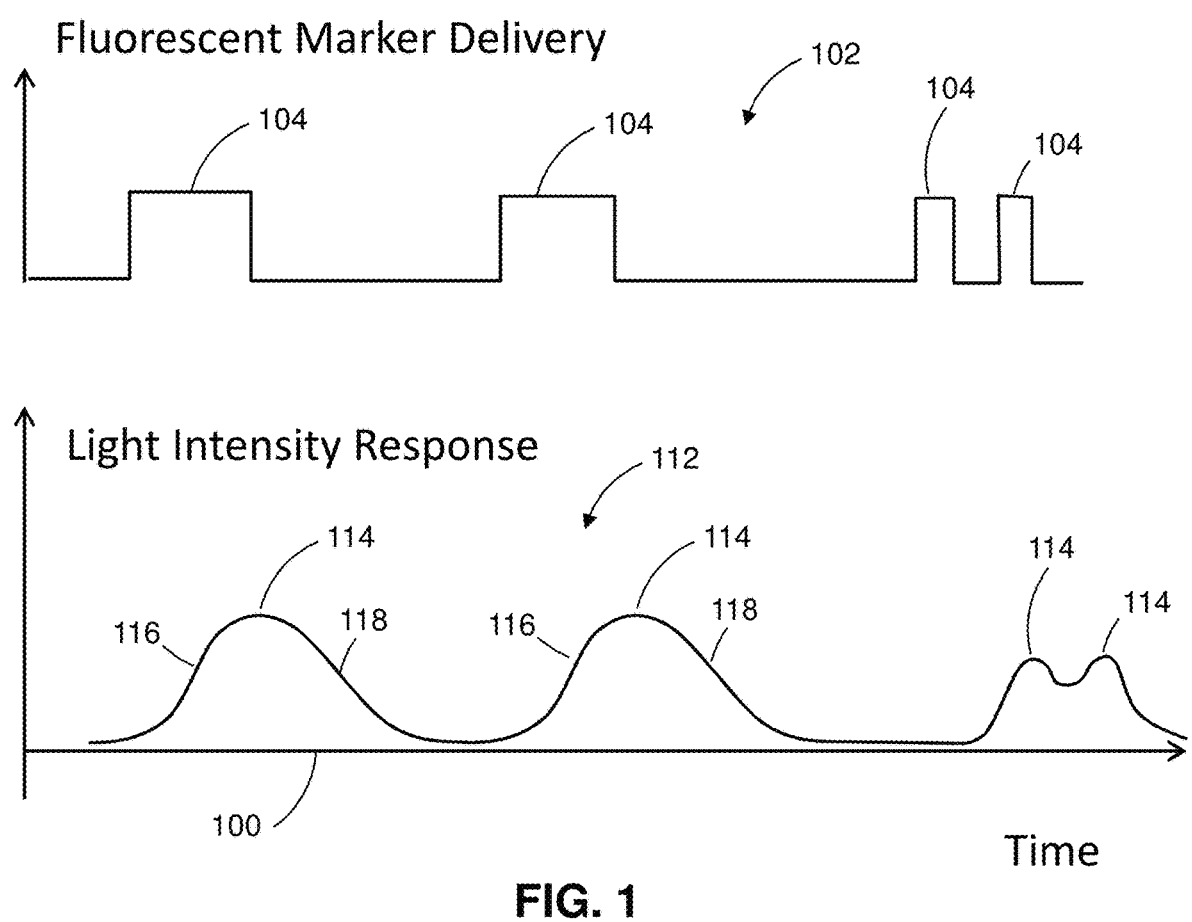
FIG. 1 shows a fluorescent marker delivery time plot in a fluid stream and a corresponding response time plot of light intensity measured downstream in a fixed field of view according to at least one embodiment.

These descriptions are presented with sufficient details to provide an understanding of one or more particular embodiments of broader inventive subject matters. These descriptions expound upon and exemplify particular features of those particular embodiments without limiting the inventive subject matters to the explicitly described embodiments and features. Considerations in view of these descriptions will likely give rise to additional and similar embodiments and features without departing from the scope of the inventive subject matters. Although the term "step" may be expressly used or implied relating to features of processes or methods, no implication is made of any particular order or sequence among such expressed or implied steps unless an order or sequence is explicitly stated.

Any dimensions expressed or implied in the drawings and these descriptions are provided for exemplary purposes. Thus, not all embodiments within the scope of the drawings and these descriptions are made according to such exemplary dimensions. The drawings are not made necessarily to scale. Thus, not all embodiments within the scope of the drawings and these descriptions are made according to the apparent scale of the drawings with regard to relative dimensions in the drawings. However, for each drawing, at least one embodiment is made according to the apparent relative scale of the drawing.

Fluorescence based tracking according to several embodiments described herein includes the providing of a marker such as a glowing dye into a fluid stream, such as a bloodstream, and making measurements and generating imagery based on the arrival, movement, and departure of the marker downstream as detected by sensor(s) to characterize the flow of the fluid stream and vessels or structures within which the flow travels. The marker is provided into a fluid stream for example by direct injection or via a port as discrete bolus deliveries separated over time. A bolus refers to the administration of a discrete amount of a fluid substance, in this case the marker into a bodily fluid stream such as blood, in order to provide a concentration of the substance to gain a response. A bolus can be delivered by active pumping or by passive gravity based delivery such as via an intravenous drip line. In at least one embodiment, a central line delivery arrangement is used, in which a port is placed in fluid communication with the subclavian vein and bolus deliveries are injected into the port. The dye briefly fluoresces when excited by an illumination source that emits a particular range of wavelengths. The dye is illuminated over the Region of Interest (ROI) where imaging of the fluorescence is also performed.

A field of view monitoring is established by placement of a sensor, such as a high speed camera, at a region of interest. The field of view can be established and held generally fixed as the marker enters and traverses the field of view of a high-speed camera sensitive to the light emitted by the marker. Time characteristics of the light output of the marker traversing the field of view can be deducted from the light output intensity as recorded by the camera. A field of view may be established for example at the heart or other organ where flow diagnostics are wanted.

The visual response in the field of view indicates presence of the marker, with the intensity of the light response being correlated with the time evolving concentration of the marker in the stream as the marker diffuses and travels with the host fluid. The light intensity in the field of view may typically have both rise and fall characteristics. The rise characteristics correspond to the arrival and increasing concentration of the marker in the field of view. The fall characteristics correspond to the departure or diffusion of the marker and/or the reduction of its light output. In the case of a dye marker in a blood stream as injected by a bolus, rise time may be faster generally than fall time such that response time curves typically show steeper climbs than falls.

FIG. 1 shows a fluorescent marker delivery time plot 102 in a fluid stream and a corresponding response time plot 112 of light intensity measured downstream in a fixed field of view according to at least one embodiment. The plots 102 and 112 are shown on a common time axis 100. The delivery time plot 102 records several bolus deliveries 104 as step functions separated in time. The response plot 112 records the corresponding response functions 114 of light intensity in a field of view downstream from the marker delivery location into a fluid stream. Each response function 114 is shown as a wave or envelope having a rise side 116 representing the arrival of the marker in the field of view, and a fall side 118 indicating the departure or diffusion of the marker and/or the reduction of its light output. In order to correlate bolus deliveries and data acquisition, a marker delivery system in at least one embodiment includes a controller and a delivery pump in wired or wireless communication. A data acquisition system including the camera and a computing device for recording, analyzing and visualizing the data and/or field of view are also in communication with the controller in at least one embodiment.

The time of initiation, delivered volume, and duration of each bolus delivery can be controlled. The time interval between consecutive bolus deliveries is also controlled. Thus, multiple parameters for bolus delivery can be adjusted to ultimately query and determine varied flow characteristics within a region of interest subjected to field of view monitoring. Shorter time gaps can be used for slower moving fluids and longer time gaps can be used for faster moving fluids within the region of interest. Injection times can be varied to address different anatomical depths and tissue surface barriers.

In at least one embodiment, as the marker from a bolus delivery enters an established field of view, the light response of a bolus is captured by a high speed camera. The time domain dynamics of the light response is analyzed to arrive at velocity vectors representing movement of the host fluid in the field of view. Several embodiments of generating velocity vectors using the data from fluorescence based tracking are described in the following with reference to FIGS. 2-5. In each, a video including multiple frames (images) taken of a region of interest is analyzed to track pixels in or across the field of view.

Figure 2:
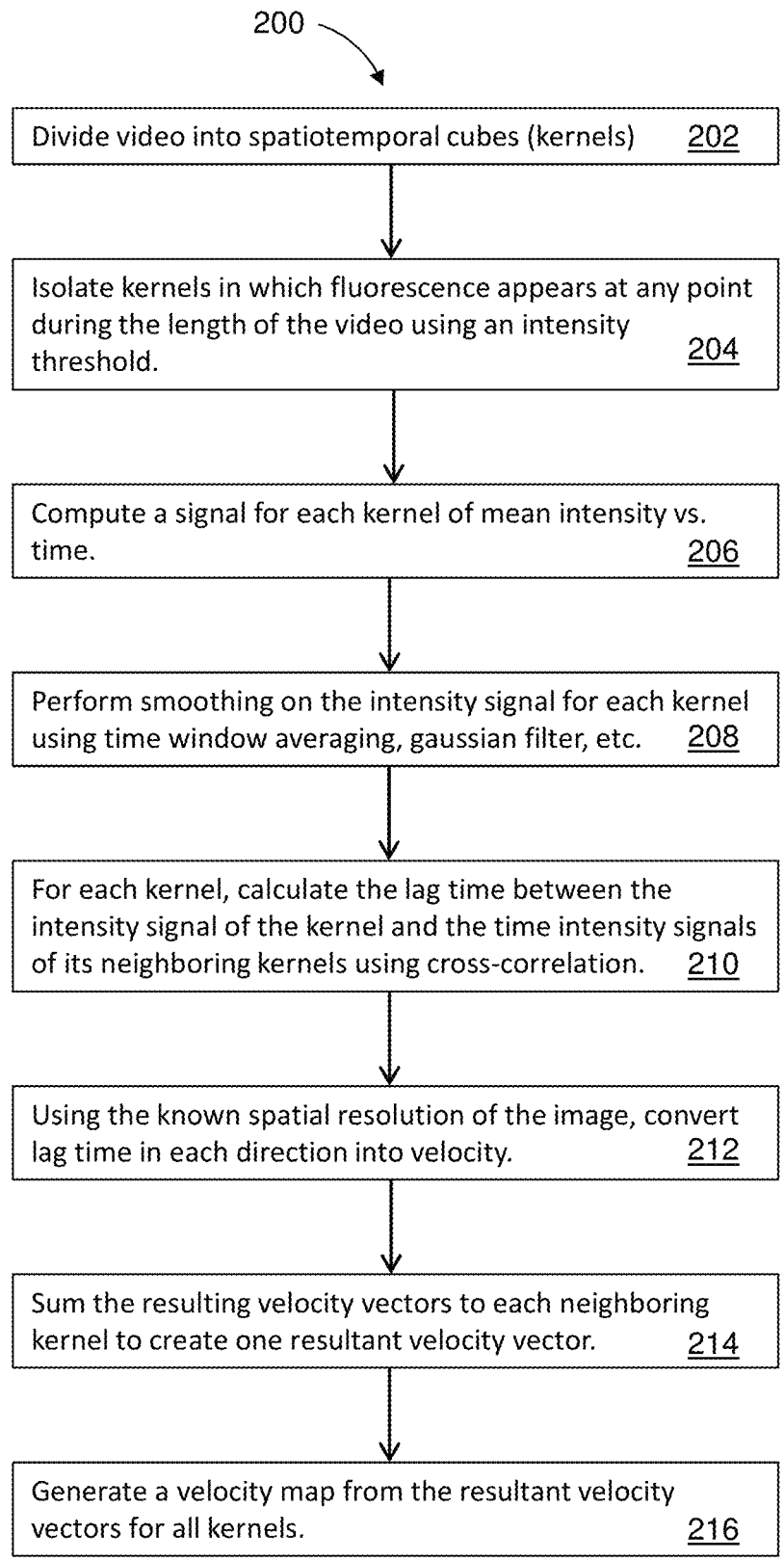
FIG. 2 shows a flowchart representing a method, according to at least one embodiment, of generating a velocity vector map using a cross correlation technique.

A method 200 of generating a velocity vector map using a cross correlation technique, according to at least one embodiment, is represented as a flow chart in FIG. 2. In step 202, divide the video into spatiotemporal cubes, which are termed "kernels" in these descriptions. In step 204, which is optional, isolate kernels in which fluorescence appears at any point during the length of the video using an intensity threshold. In step 206, compute a signal for each kernel of mean intensity vs. time. The signal may be 1D, 2D, or 3D. Vessel(s) may cross under other vessel(s) and at different angles, and multiple perspectives from different cameras can be used. The potential use of coded apertures is within the scope of these descriptions. In step 208, which is optional, perform smoothing on the intensity signal for each kernel using time window averaging, Gaussian filter, etc. In step 210, for each kernel, calculate the lag time between the intensity signal of the kernel and the time intensity signals of its neighboring kernels using cross-correlation. In step 212, using the known spatial resolution of the image, convert lag time in each direction into velocity. In step 214, sum the resulting velocity vectors to each neighboring kernel to create one resultant velocity vector. In step 216, generate a velocity map from the resultant velocity vectors for all kernels.

Figure 3:
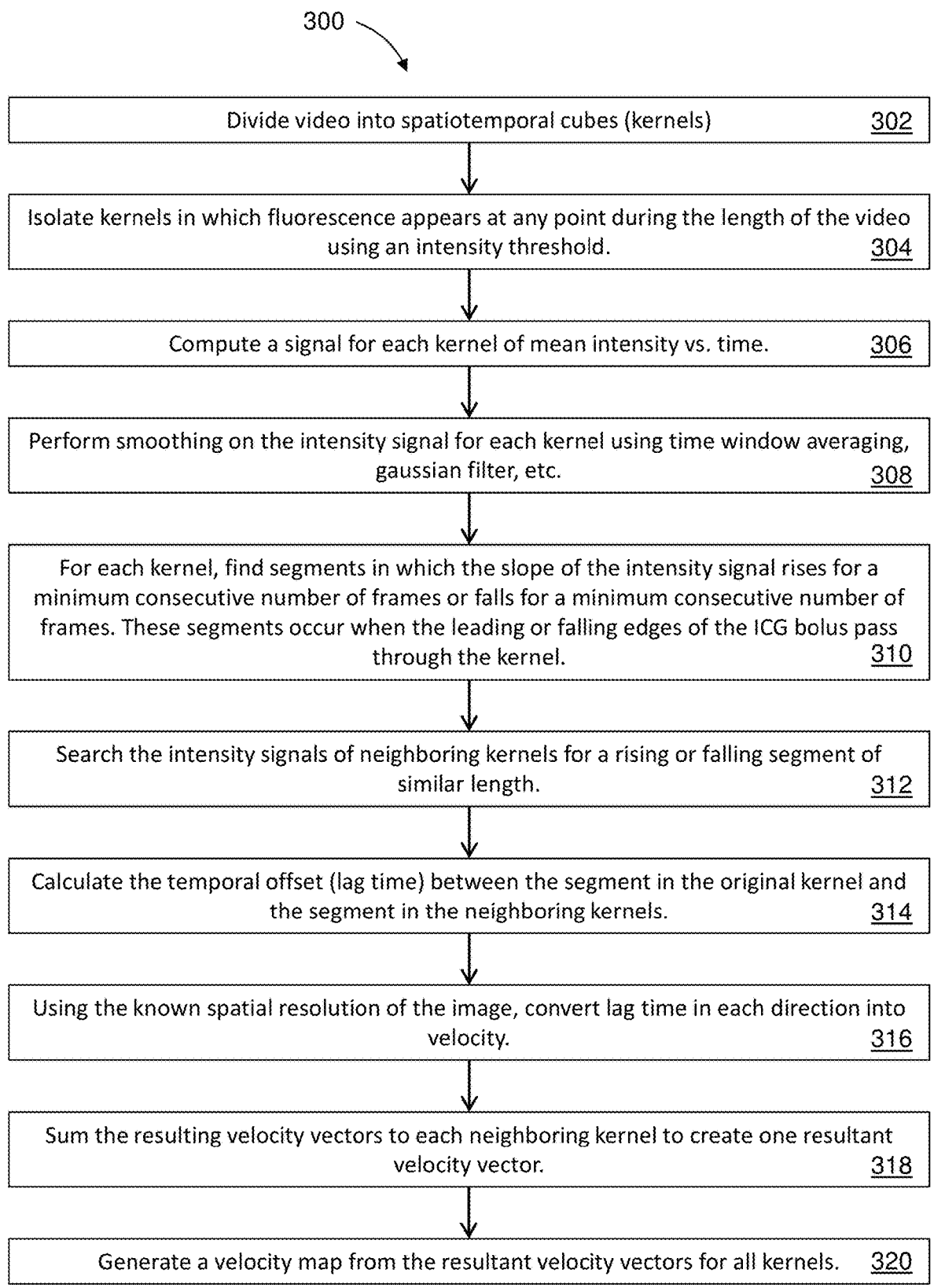
FIG. 3 shows a flowchart representing a method, according to at least one embodiment, of generating a velocity vector map using leading and falling edge considerations.

A method 300 of generating a velocity vector map using leading and falling edge considerations, according to at least one embodiment, is represented as a flow chart in FIG. 3. In step 302, divide video into kernels. In step 304, which is optional, isolate kernels in which fluorescence appears at any point during the length of the video using an intensity threshold. In step 306, compute a signal for each kernel of mean intensity vs. time. As described above with reference to step 206 of FIG. 2, the signal may be 1D, 2D, or 3D. In step 308, which is optional, perform smoothing on the intensity signal for each kernel using time window averaging, Gaussian filter, etc. In step 310, for each kernel, find segments in which the slope of the intensity signal rises for a minimum consecutive number of frames or falls for a minimum consecutive number of frames. These segments occur when the leading or falling edges of the ICG (fluorescein or other glow dye) bolus pass through the kernel. In step 312, search the intensity signals of neighboring kernels for a rising or falling segment of similar length. In step 314, calculate the temporal offset (lag time) between the segment in the original kernel and the segment in the neighboring kernels. In step 316, using the known spatial resolution of the image, convert lag time in each direction into velocity. In step 318, sum the resulting velocity vectors to each neighboring kernel to create one resultant velocity vector. In step 320, generate a velocity map from the resultant velocity vectors for all kernels.

Figure 4:
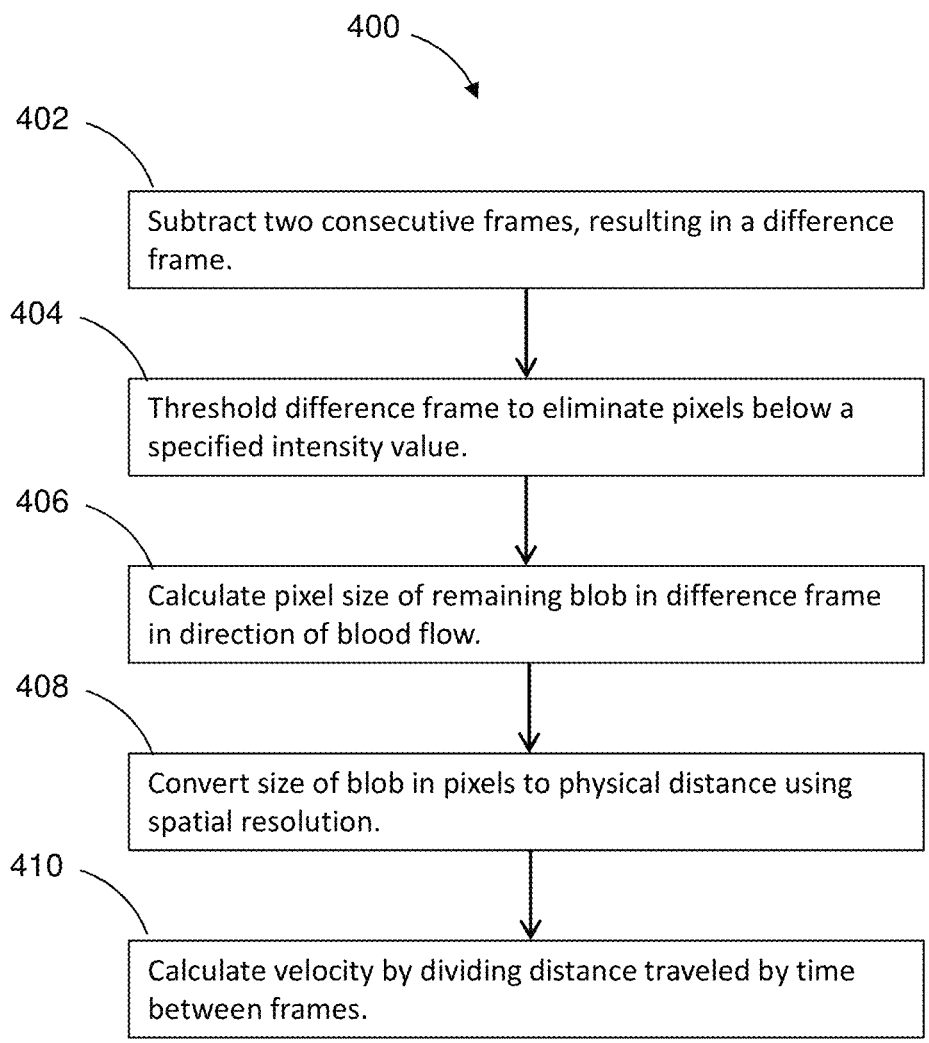
FIG. 4 shows a flowchart representing a method, according to at least one embodiment, of generating a velocity vector map using subtraction.

A method 400 of generating a velocity vector map using subtraction, according to at least one embodiment, is represented as a flow chart in FIG. 4. In step 402, subtract two consecutive frames, resulting in a difference frame. In step 404, threshold difference frame to eliminate pixels below a specified intensity value. In step 406, calculate pixel size of a remaining blob in the difference frame in the direction of blood flow. In step 408, convert size of blob in pixels to physical distance using spatial resolution. In step 410, calculate velocity by dividing distance traveled by time between frames.

Figure 5:
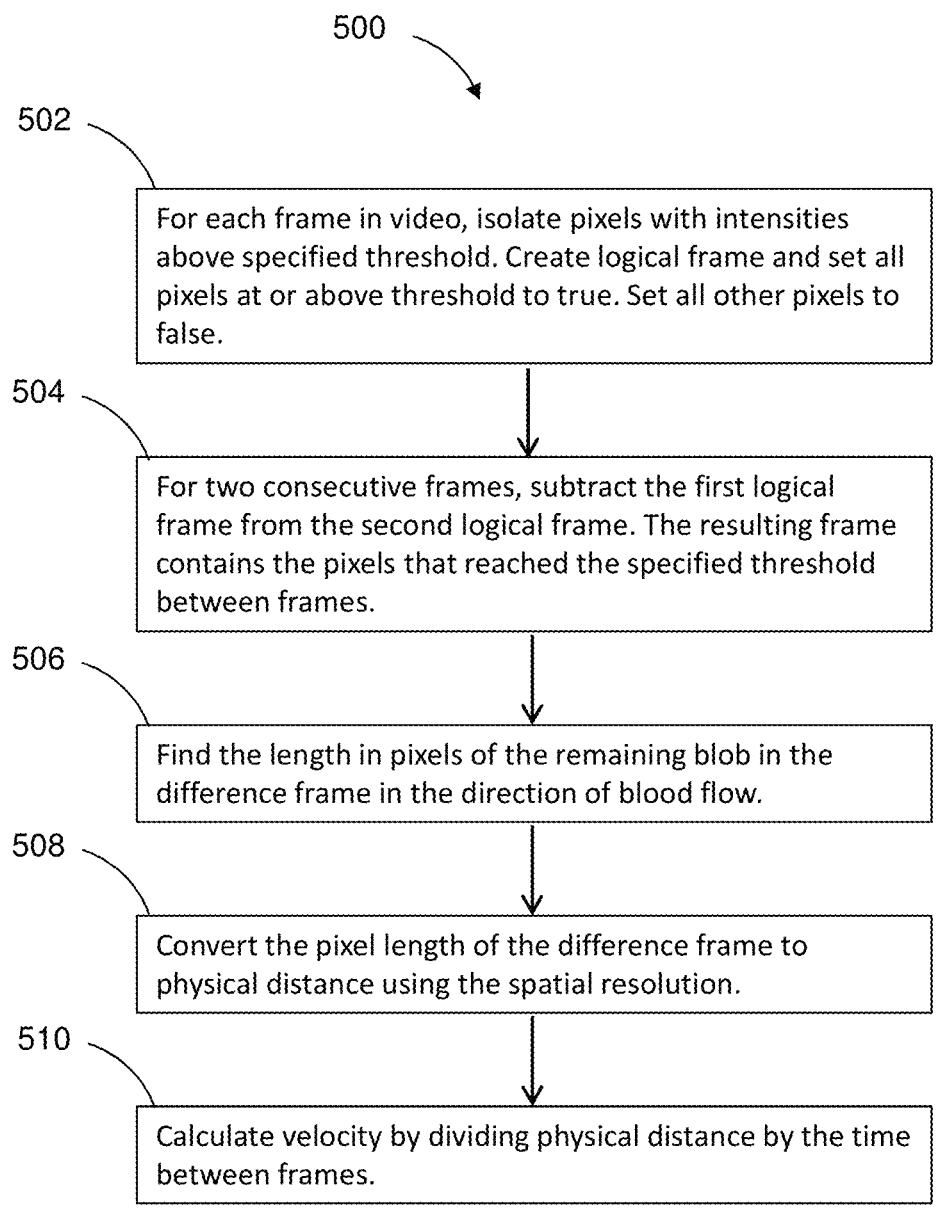
FIG. 5 shows a flowchart representing a method, according to at least one embodiment, of generating a velocity vector map using thresholding.

A method 500 of generating a velocity vector map using thresholding, according to at least one embodiment, is represented as a flow chart in FIG. 5. In step 502, for each frame in video, isolate pixels with intensities above specified threshold. Create logical frame and set all pixels at or above threshold to true. Set all other pixels to false. In step 504, for two consecutive frames, subtract the first logical frame from the second logical frame. The resulting frame contains the pixels that reached the specified threshold between frames. In step 506, find the length in pixels of the remaining blob in the difference frame in the direction of blood flow. In step 508, convert the pixel length of the difference frame to physical distance using the spatial resolution. In step 510, calculate velocity by dividing physical distance by the time between frames.

Figure 6:
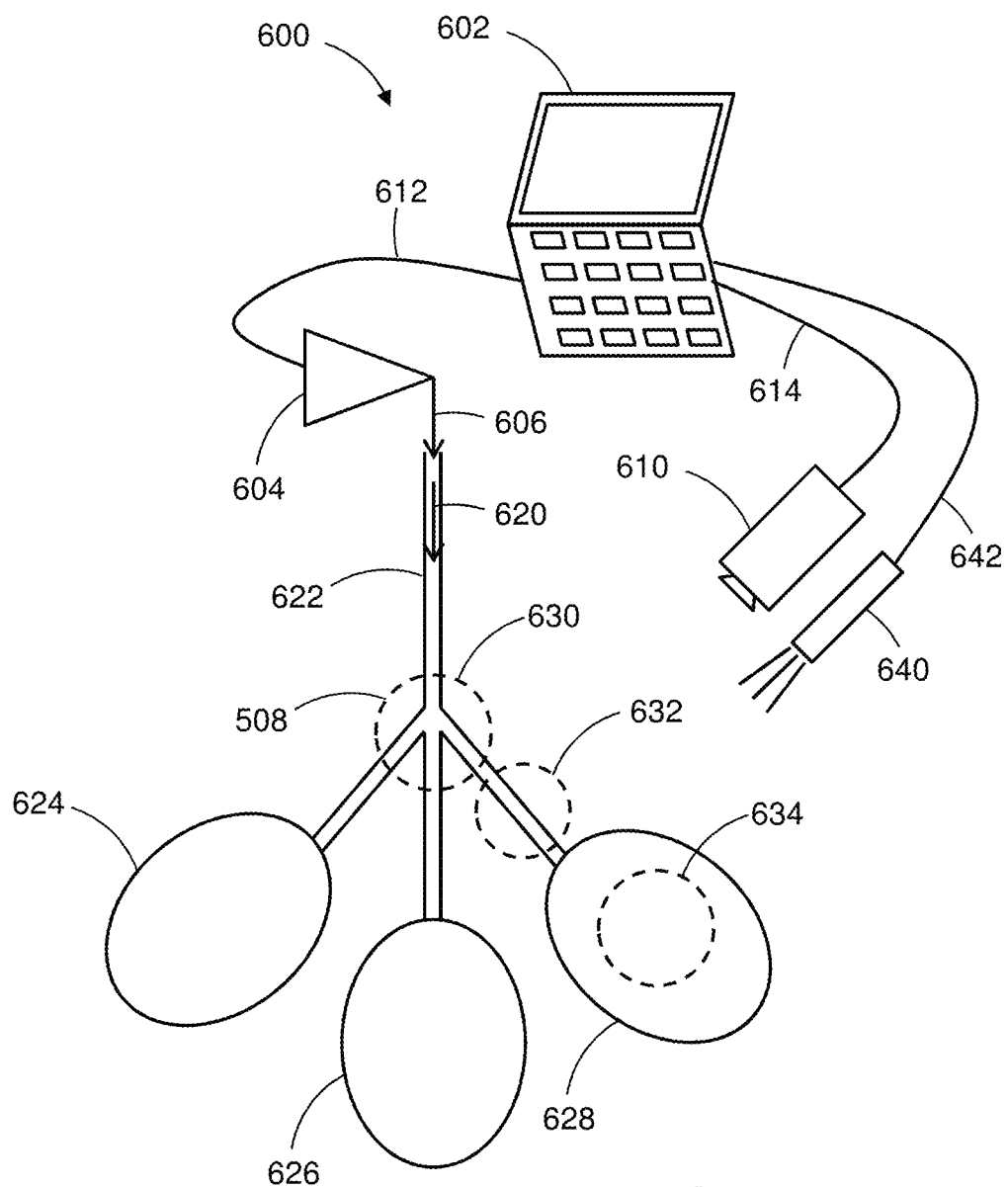
FIG. 6 shows a system, according to at least one embodiment, by which at least the methods of FIGS. 2-5 are implemented.

FIG. 6 shows a system 600, according to at least one embodiment, by which at least the methods of FIGS. 2-5 are implemented. The system 600 includes a computing device 602, a delivery apparatus 604 configured to provide a light-emitting marker 606 into a bodily fluid stream, and a sensor 610 configured to monitor a region of interest traversed by the bodily fluid stream. The computing device 602 records data generated by the sensor 610, determines time characteristics of the recorded data; and calculates flow characteristics based on the time characteristics.

The computing device 602 is illustrated as a laptop or other personal computer. Other computing devices including local and remote servers are within the scope of these descriptions. The delivery apparatus 604 provides a light-emitting marker 606. The delivery apparatus 604 is in communication with and/or under the control of the computing device 602. The delivery apparatus 604 may include a powered pump or a gravity based arrangement. The light-emitting marker 606 may be delivered to the bodily fluid stream 620 via a catheter, an intravenous drip line, a central line delivery, or other needle or port device. The delivery apparatus 604 delivers the light-emitting marker 606 in discrete bolus deliveries separated over time. The light-emitting marker 606 may include Indocyanine green (ICG), Fluorescein or other glow dye. Two or more dyes, each having a different respective color, may be used. For example, each bolus of two or more may include a different dye and thus the presence and response of each can be determined separately by color distinction.

The bodily fluid stream 620 in FIG. 6 is represented as flowing along a blood vessel or other biological conduit 622. Several downstream organs or tissue areas 624, 626 and 628 are represented. By placement and selection of field of view of the sensor 610, a region of interest can be selected for observation downstream of the bodily fluid stream 620 carrying with it the light-emitting marker 606. The sensor 610 monitors for fluorescence or other indication of the presence of the light-emitting marker 606 in the selected field of view. The sensor 610 can be a high-speed and high-resolution camera for example.

Several fields of view are represented. In a first exemplary field of view 630, the sensor 610 observes an area where the bodily fluid stream 620 is divided into several downstream flows. In a second exemplary field of view 632, the sensor 610 observes an area downstream of the division to isolate monitoring to a single branch of downstream flow. In a third exemplary field of view 634, the sensor 610 observes a particular organ or tissue area 628. These examples represent that a user such as a physician can deliver a light-emitting marker 606 at any selected location and then observe the time evolving arrival and dispersion or other activity of the marker downstream of the selected location at any selected field of view. In at least one embodiment, a central line delivery arrangement is used, in which a port is placed in fluid communication with the subclavian vein and bolus deliveries of the light-emitting marker 606 are injected into the port.

The delivery apparatus 604 and sensor 610 are shown as connected to the computing device 602 by respective cables 612 and 614, however wireless connections may be used as well. The light-emitting marker 606 briefly fluoresces when excited by an illumination source 640 that emits a particular range of wavelengths upon the region of interest within the field of view of the sensor 610. The illumination source 640 is also shown as connected to the computing device 602 by a cable 642, however a wireless connection may be used as well. The computing device correlates activations of the delivery apparatus 604, the illumination source 640, and the sensor 610, and collects data from the sensor 610 as the light-emitting marker 606 in the field of view responds to the excitation from the illumination source 640.

In various embodiments, the computing device 602 is configured to record data generated by the sensor 610; determine time characteristics of the recorded data; and calculate flow characteristics based on the time characteristics. Further embodiments and examples of fluorescence based imaging and data analysis conducted by the computing device 602 are described above with reference to FIGS. 2-5.

Particular embodiments and features have been described with reference to the drawings. It is to be understood that these descriptions are not limited to any single embodiment or any particular set of features, and that similar embodiments and features may arise or modifications and additions may be made without departing from the scope of these descriptions and the spirit of the appended claims.

What is claimed is:

1. A system for fluorescence based tracking of a light-emitting marker in a fluid stream, the system comprising:
   a delivery apparatus configured to provide a light-emitting marker into a fluid stream;
   a camera configured to monitor a region of interest traversed by the fluid stream; and
   a computing device configured to:
      record motion video data generated by the camera;
      divide the motion video data into kernels;
      identify which of the kernels receive some portion of the light-emitting marker using an intensity threshold;
      determine time characteristics of the recorded data; and
      calculate flow characteristics based on the time characteristics,
   wherein the computing device is further configured to:
      compute, for each identified kernel, an intensity signal data set comprising information of mean light intensity versus time;
      perform smoothing on each intensity signal data set, and
      calculate a lag time between the intensity signal data sets of neighboring identified kernels using cross-correlation.

2. The system according to claim 1, wherein the computing device is further configured to
   use spatial resolution and the lag time to calculate velocity characteristics.

3. The system according to claim 2, wherein the computing device is further configured to sum the velocity characteristics of neighboring kernels to create resultant velocity characteristics, and generate a velocity map from the resultant velocity characteristics for all kernels.

4. The system according to claim 3, wherein the computing device is further configured
for each particular identified kernel, to:
find segments in which a slope of the intensity signal data set rises for a minimum consecutive number of frames or falls for a minimum consecutive number of frames, which segments occur when a leading edge or falling edge of a portion of the light-emitting marker passes through the identified kernel.

5. The system according to claim 4, wherein the computing device is further configured
for each particular identified kernel, to:
search the intensity signal data sets of neighboring identified kernels for a rising or falling segment of similar length; and
calculate a lag time between segments in the particular identified kernel and segments in the neighboring identified kernel.

6. The system according to claim 5, wherein the computing device is further configured to:
divide the motion video data into frames each comprising pixels;
identify which of the pixels receive some portion of the light-emitting marker using an intensity threshold;
calculate a difference frame by subtracting a frame of the motion video data from a consecutive frame of the motion video data;
apply a threshold to the difference frame to eliminate pixels therein below a specified intensity value;
calculate a pixel size of a remaining blob in the difference frame in a direction of fluid flow;
calculate a size of the remaining blob using the pixel size and a spatial resolution; and
calculate a velocity by using a distance traveled by the remaining blob and a time between frames.

7. The system according to claim 6, wherein the computing device is further configured to:
create a logical frame in which a respective indicator for each pixel can be set as true or false;
set the indicators of the identified pixels as true;
set the indicators of all other pixels as false;
calculate a difference frame by subtracting a first logical frame from a second logical frame such that the difference frame comprises pixels that reached the specified threshold after a time of the first logical frame;
find length in pixels of the remaining blob in the difference frame in a direction of fluid flow;
convert the length in pixels of the difference frame to physical distance using the spatial resolution; and
calculate velocity by dividing the physical distance by a time between frames.

8. The system according to claim 1, wherein the computing device performs smoothing on each intensity signal data set by time window averaging.

9. The system according to claim 1, wherein the computing device performs smoothing on each intensity signal data set by using a filter.

10. A method of fluorescence based tracking of a light-emitting marker in a fluid stream, the method comprising:
monitoring, with a camera, a region of interest traversed by a fluid stream into which a light emitting marker has been introduced;
recording motion video data generated by the camera;
dividing the motion video data into kernels;
identifying which of the kernels receive some portion of the light-emitting marker using an intensity threshold;
determining time characteristics of the recorded data;
calculating flow characteristics based on the time characteristics;
computing, for each identified kernel, an intensity signal data set comprising information of mean light intensity versus time;
performing smoothing on each intensity signal data set; and
calculating a lag time between the intensity signal data sets of neighboring identified kernels using cross-correlation.

11. The method according to claim 10, further comprising:
using a spatial resolution and the lag time, calculating velocity characteristics;
summing the velocity characteristics of neighboring kernels to create a resultant velocity characteristic; and
generating a velocity map from the resultant velocity characteristics for all kernels.

12. The method according to claim 11, wherein performing smoothing on each intensity signal data set comprises time window averaging.

13. The method according to claim 11, wherein performing smoothing on each intensity signal data set comprises using a filter.

14. The method according to claim 11, further comprising:
for each particular identified kernel, finding segments in which a slope of the intensity signal data set rises for a minimum consecutive number of frames or falls for a minimum consecutive number of frames, which segments occur when a leading edge or falling edge of a portion of the light-emitting marker passes through the identified kernel;
searching the intensity signal data sets of neighboring identified kernels for a rising or falling segment of similar length; and
calculating a lag time between segments in the particular identified kernel and segments in the neighboring identified kernels.

15. A method of fluorescence based tracking of a light-emitting marker in a fluid stream, the method comprising:
monitoring, with a camera, a region of interest traversed by fluid stream into which a light-emitting marker has been introduced;
recording motion video data generated by the sensor;
dividing the motion video data into frames each comprising pixels;
identifying which of the pixels receive some portion of the light-emitting marker using an intensity threshold;
calculating a difference frame by subtracting a frame of the motion video data from a consecutive frame of the motion video data;
applying a threshold to the difference frame to eliminate pixels therein below a specified intensity value;
calculating a pixel size of a remaining blob in the difference frame in a direction of fluid flow;
calculating a size of the remaining blob using the pixel size and a spatial resolution; and
calculating a velocity by using a distance traveled by the remaining blob and a time between frames.

16. A method according to claim 15, further comprising:
creating a logical frame in which a respective indicator for each pixel can be set as true or false;
setting the indicators of the identified pixels as true;
setting the indicators of all other pixels as false;
calculating a difference frame by subtracting a first logical frame from a second logical frame such that the difference frame comprises pixels that reached the specified threshold after a time of the first logical frame;
finding length in pixels of a remaining blob in the difference frame in a direction of fluid flow;
converting the length in pixels of the difference frame to physical distance using the spatial resolution; and
calculating velocity by dividing the physical distance by a time between frames.

* * * * *